US010466158B2

(12) United States Patent
Otsuka et al.

(10) Patent No.: US 10,466,158 B2
(45) Date of Patent: Nov. 5, 2019

(54) MICROPARTICLE SORTING APPARATUS AND DELAY TIME DETERMINATION METHOD

(71) Applicants: SONY CORPORATION, Minato-Ku, Tokyo (JP); SONY CORPORATION OF AMERICA, New York, NY (US)

(72) Inventors: Fumitaka Otsuka, San Jose, CA (US); Michael Zordan, Boulder Creek, CA (US); Akiko Tsuji, Machida (JP); Yuya Suzuki, Kanagawa (JP); Masashi Kimoto, Oota-ku (JP)

(73) Assignees: Sony Corporation, Tokyo (JP); Sony Corporation of America, New York, NY (US)

( * ) Notice: Subject to any disclaimer, the term of this patent is extended or adjusted under 35 U.S.C. 154(b) by 0 days.

(21) Appl. No.: 15/919,012

(22) Filed: Mar. 12, 2018

(65) Prior Publication Data

US 2018/0292304 A1 Oct. 11, 2018

Related U.S. Application Data

(60) Provisional application No. 62/484,153, filed on Apr. 11, 2017.

(51) Int. Cl.
*G01N 15/14* (2006.01)

(52) U.S. Cl.
CPC ..... *G01N 15/1436* (2013.01); *G01N 15/1425* (2013.01); *G01N 2015/144* (2013.01); *G01N 2015/149* (2013.01)

(58) Field of Classification Search
CPC .......... G01N 15/1404; G01N 15/1434; G01N 15/1459; G01N 15/1484; G01N 2015/1409; G01N 2015/1422; G01N 2015/1481; B01L 3/502761; B01L 3/502766
See application file for complete search history.

(56) References Cited

U.S. PATENT DOCUMENTS 3,710,933 A 1/1973 Fulwyler et al.
5,916,449 A * 6/1999 Ellwart .............. G01N 15/1404
209/3.2

(Continued)

OTHER PUBLICATIONS

Federal Institute of Industrial Property, International Search Report for PCT/US2018/025919, dated Aug. 2, 2018.

(Continued)

*Primary Examiner* — Joseph C Rodriguez
(74) *Attorney, Agent, or Firm* — Ice Miller LLP

(57) ABSTRACT

A microparticle sorting apparatus includes a detection unit which detects microparticles flowing through a flow path; an imaging device which images a droplet containing the microparticles which is discharged from an orifice provided on an edge portion of the flow path; a charge unit which applies a charge to the droplets; and a control unit which determines a delay time as from a time that the microparticles are detected by the detection unit to the time at which the sum of intensity of an image region imaged by the imaging device reaches a maximum, making it possible for the charge unit to apply a charge to the microparticles once the delay time has lapsed after the microparticles are detected by the detection unit.

20 Claims, 11 Drawing Sheets

(56) References Cited

U.S. PATENT DOCUMENTS

| | | | | |
|---|---|---|---|---|
| 6,079,836 | A * | 6/2000 | Burr | G01N 15/1404 356/335 |
| 8,795,500 | B2 | 8/2014 | Shinoda | |
| 9,034,259 | B2 * | 5/2015 | Kanda | G01N 15/14 422/50 |
| 9,134,220 | B2 * | 9/2015 | Malachowski | G01N 15/1475 |
| 9,255,874 | B2 * | 2/2016 | Sharpe | G01N 15/1404 |
| 9,784,660 | B2 * | 10/2017 | Otsuka | B07C 5/3422 |
| 9,915,935 | B2 * | 3/2018 | Muraki | G01N 15/1434 |
| 9,958,375 | B2 * | 5/2018 | Muraki | B03C 7/003 |
| 9,964,968 | B2 * | 5/2018 | Sharpe | G05D 21/02 |
| 2013/0256136 | A1 | 10/2013 | Muraki et al. | |
| 2014/0176704 | A1 * | 6/2014 | Perrault, Jr. | G01N 15/1404 348/135 |
| 2015/0057787 | A1 | 2/2015 | Muraki et al. | |

OTHER PUBLICATIONS

Federal Institute of Industrial Property, Written Opinion of the International Searching Authority for PCT/US2018/025919, dated Aug. 2, 2018.

* cited by examiner

MICROPARTICLE SORTING APPARATUS AND DELAY TIME DETERMINATION METHOD

CROSS REFERENCE TO RELATED APPLICATION

The present application is a nonprovisional patent application, which claims the priority benefit of U.S. Provisional Application Ser. No. 62/484,153, filed on Apr. 11, 2017, the text and drawings of which are hereby incorporated by reference in its entirety.

BACKGROUND

The present technology relates to a microparticle sorting apparatus and a delay time determination method in the microparticle sorting apparatus. More specifically, the present technology relates to a microparticle sorting apparatus or the like which automatically determines the delay time.

In the related art, there is a microparticle sorting apparatus (for example, a flow cytometer) which optically, electrically, or magnetically detects the characteristics of microparticles such as cells, then separates and collects only the microparticles which have predetermined characteristics.

In cell separation in a flow cytometer, first, a droplet stream (a laminar flow of a sample fluid containing cells and a sheath fluid) is generated from an orifice formed in the flow cell, the fluid stream is made into droplets by applying oscillation to the orifice, and a charge is applied to the droplets. Furthermore, the movement direction of the droplets containing the cells discharged from the orifice is electrically controlled and the target cells having the desired characteristics and the other non-target cells are collected in separate collection containers.

For example, Japanese Unexamined Patent Application Publication No. 2010-190680 discloses, as a microchip-type flow cytometer, a microparticle sorting apparatus including: a microchip on which a flow path through which a fluid containing microparticles flows, and an orifice which discharges a fluid which flows through a flow path to a space outside of the chip are installed; an oscillating element for making a fluid into droplets in the orifice and discharging them; an electrical charging means for applying a charge to the discharged droplets; an optical detection means for detecting the optical characteristics of the microparticles flowing though the flow path; an electrode couple installed opposing one another to interpose the moving droplets; and two or more containers which collect the droplets which passed between the opposing electrodes".

In addition, Japanese Unexamined Patent Application Publication (Translation of PCT Application) No. 2007532874 discloses a method in which control is performed on the operation of a flow cytometer which is capable of confirming whether or not the droplets have been sorted into an intended flow path by disposing auxiliary lighting and a detection unit in the position at which the droplets break off from the fluid (hereinafter, referred to as the break-off point). By ascertaining the break-off point in this manner, it is possible to ascertain the delay time from when the microparticles, which are cells or the like, are detected until the droplets containing the cells or the like reach the break-off point, and it is possible to apply a charge to the droplets containing the microparticles which are detected based on the delay time.

SUMMARY

However, the break-off point fluctuates according to the discharge conditions of the droplets and the like, and therefore the delay time also fluctuates. In addition, it is difficult to sufficiently ascertain an accurate timing to apply a charge to the droplets containing the microparticles by only ascertaining the break-off point. Therefore, the correct charge is applied to the droplets which contain the microparticles, but in the end, methods have mostly been adopted in which the user visually discriminates whether the droplets have been allotted to the desired collection container or not by observing the droplets, to which a charge is applied, on a preparation. Such methods demanded that the user have a mastery of the technology, and there are problems with the reliability and stability.

Therefore, it is desirable to provide a microparticle sorting apparatus which is capable of automatically, simply, and accurately applying a charge to droplets.

In an embodiment, a microparticle sorting apparatus is disclosed. The microparticle sorting apparatus includes a detector configured to detect microparticles flowing through a flow path and an imaging device configured to obtain an image of a droplet containing at least one of the microparticles where the droplet is discharged from an orifice provided on the flow path. The microparticle sorting apparatus further includes a controller. The controller is configured to control the imaging device to obtain the image, where the image has a first and second image region and the first and second image region each have a plurality of sub-areas. The controller is further configured to determine an intensity of image brightness for each of said sub-areas and add the intensity of the image brightness for each of the sub-areas within each of the first and second image regions to obtain a sum of intensity of each of the first image region and the second image region. The controller is further configured to determine a delay time by examining the sum of intensity of the first and second image regions and identifying a maximum sum of intensity characteristic and set a timing for applying a charge to the droplets based on the delay time In another embodiment, the sum of intensity of each of the first and second image regions is determined at a plurality of different times. In yet another embodiment the plurality of different times is based on a droplet clock cycle and spans three droplet clock cycles. In yet another embodiment each droplet clock cycle consists of three hundred and sixty degrees and wherein the plurality of different times occur at twenty degree intervals. In yet another embodiment plurality of different times occur at forty degree intervals. In yet another embodiment, the plurality of different times occur at sixty degree intervals.

In another embodiment the image further includes a third image region having a plurality of sub-areas, and the controller is additionally configured to determine an intensity of image brightness for each of the sub-areas in the third image region. The controller is also configured to add the intensity of the image brightness for each of the sub-areas within the third image region to obtain a sum of intensity of the third image region and determine the delay time by examining the sum of intensity of the third image region.

In another embodiment, the maximum sum of intensity characteristic is determined by computing a first image region ratio:

$$\text{first image region ratio} = \left(\frac{\text{first image region sum of intensity}}{\text{first + second + third image region sums of intensity}}\right).$$

In another embodiment, the first image region is associated with a last attached droplet. In yet another embodiment, the first image region is associated with a droplet following a last attached droplet in a droplet stream. In yet another embodiment, the second image region is adjacent to the first image region and the third image region is adjacent to either the second image region or the first image region.

In another embodiment, the maximum sum of intensity characteristic is determined by minimizing any of the sum of intensity of the second image region, the sum of intensity of the third image region, or both. In yet another embodiment, the maximum sum of intensity characteristic is determined by maximizing the sum of intensity of the first image region.

In an embodiment, a microparticle sorting apparatus is disclosed, comprising a detector configured to detect microparticles flowing through a flow path, an imaging device configured to obtain an image of a droplet containing at least one of the microparticles, where the droplet is discharged from an orifice provided on the flow path creating a droplet stream, and a controller configured to. The controller is configured to control the imaging device to obtain the image, where the image includes a first image region having a first plurality of sub-areas, a second image region having a second plurality of sub-areas, and a third image region having a third plurality of sub-areas. The controller is also configured to obtain the image at a plurality of different times and for each of the plurality of different times, determine an intensity of brightness for each of the first plurality of sub-areas, each of the second plurality of sub-areas, and each of the third plurality of sub-areas. The controller is further configured to add the intensity of brightness for each of the first plurality of sub-areas to obtain a first image region sum of intensity, the intensity of brightness for each of the second plurality of sub-areas to obtain a second image region sum of intensity, and the intensity of brightness for each of the third plurality of sub-areas to obtain a third image region sum of intensity, thereby obtaining a first image region sum of intensity, a second image region sum of intensity, and a third image region sum of intensity at each of the plurality of different times. The controller is further configured to determine a delay time, which is the time at which the detector detects microparticles flowing through the flow path to the time at which the first image region sum of intensity is at a maximum by determining a maximum sum of intensity characteristic and set a timing for applying a charge to the droplets based on the delay time.

In another embodiment, the delay time is based on a droplet clock cycle where the charge is applied to the last attached droplet and where +1 droplet clock cycle is added to the delay time to obtain the delay time for the last attached droplet.

A BRIEF DESCRIPTION OF THE DRAWINGS

FIG. 6A is an exemplary droplet image, FIG. 6B is an exemplary calibration image, and FIG. 6C is an exemplary representation of the LED strobe and calibration strobe in relation to the droplet clock;

FIGS. 7A and 7B represent droplet images, FIG. 7C represents a calibration image, and FIG. 7D represents the LED strobe and calibration strobe in relation to the droplet clock;

FIGS. 8A and 8B represent droplet images, FIG. 8C represents a calibration image, and FIG. 8D represents the LED strobe and calibration strobe in relation to the droplet clock;

Figure 11:
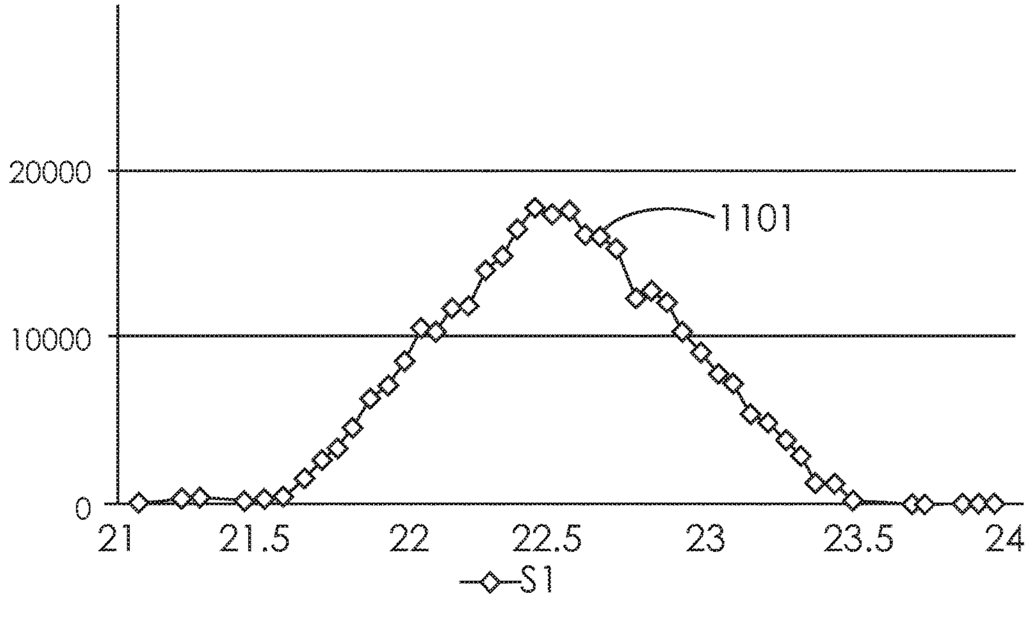
Figure 12:
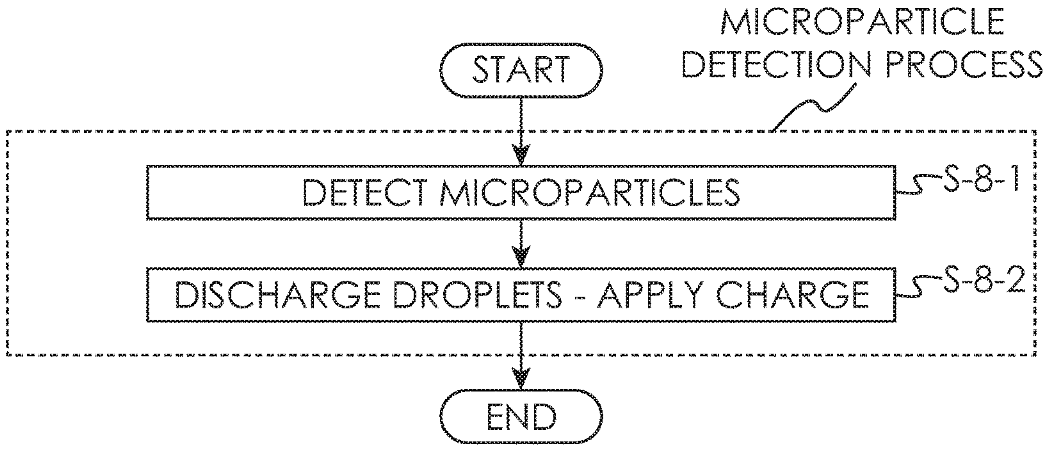

FIG. 11 is an explanatory diagram, which is a graph in which the horizontal axis is the delay time and the vertical axis is the sum of intensity of the images of the droplets imaged by the droplet camera of the flow cytometer, for illustrating an example of the delay time determination step (the third delay time determination method); and FIG. 12 is a flow diagram for illustrating the method of sorting the microparticles (the microparticle sorting step) in the flow cytometer.

DETAILED DESCRIPTION OF EMBODIMENTS

Hereafter, description will be given of favorable embodiments for realizing the present technology with reference to the drawings. Furthermore, the embodiments described below represent an example of a representative embodiment of the present technology, and the scope of the present technology is not to be interpreted narrowly according to this example. The description will be given in the following order.

1. Apparatus Configuration of Microparticle Sorting Apparatus according to Present Technology
   1-1 Charge Unit
   1-2 Microchip
   1-3 Detection Unit
   1-4 Droplet Camera
   1-5 Deflection Plate
   1-6 Collection Container
   1-7 Control Unit or Similar
2. Delay Time Determination Method in Microparticle Sorting Apparatus according to Present Technology
   2-1 Microparticle Detection Step S1
   2-2 Droplet Discharge Step S2

2-3 Droplet Imaging Step S3

2-4 Discharge Frequency Determination Step S4

2-5 Rough Delay Time Determination Step S5

2-6 Image Region Determination Step S6

2-7 Fine Delay Time Determination Step S7

2-7-1 First Fine Delay Time Determination Method 2-7-2 Second Fine Delay Time Determination Method 2-7-3 Third Fine Delay Time Determination Method 2-8 Microparticle Sorting Step S8

Figure 1:
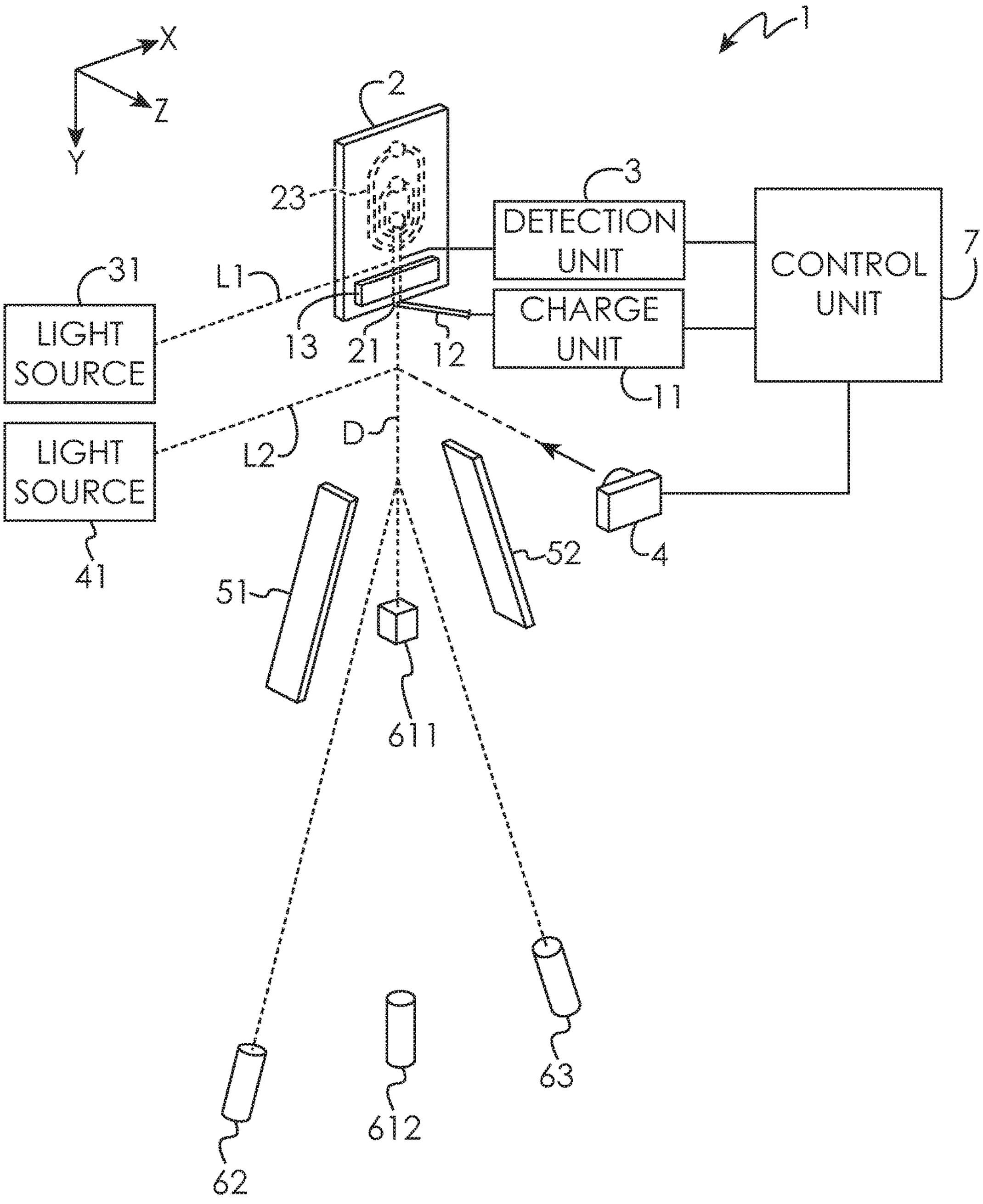
FIG. 1 is a schematic view for illustrating the configuration of the sorting system of a microparticle sorting apparatus (a flow cytometer) according to an embodiment of the present technology which is configured as a microchip-type flow cytometer.

2-8-1 Microparticle Detection Step 2-8-2 Droplet Discharge and Charge Application Step 1. Apparatus Configuration of Microparticle Sorting Apparatus According to Present Technology FIG. 1 is a schematic view for illustrating the configuration of the sorting system of the microparticle sorting apparatus 1 (hereinafter also referred to as "the flow cytometer 1") according to an embodiment of the present technology which is configured as a microchip-type flow cytometer.

1-1 Charge Unit

The flow cytometer 1 is provided with a charge unit 11 which applies a charge to the droplets discharged from the orifice 21 formed on the microchip 2. The charging of the droplets is performed by a charging apparatus 12, such as electrodes or an excitation laser (not shown), which are electrically connected to the charge unit 11. The charging apparatus 12 may gain access to the droplets through an inlet (not shown) provided in the microchip 2. Furthermore, it is sufficient for the electrodes to be inserted to a location on the microchip 2 so as to make electrical contact with the sample fluid or the sheath fluid which is pumped down the flow path. Similarly, it is sufficient for the excitation laser to be at a location on the microchip 2 so as to allow access for the laser to the sample fluid or the sheet fluid which is pumped down the flow path.

In the flow cytometer 1, it is possible for the charge unit 11 to charge the droplets containing the microparticles once the delay time has elapsed after the microparticles contained in the sample fluid are detected by a detection unit 3 described below. Here, the term "delay time" refers to the delay time from the time that the microparticles are detected by the detection unit 3 to when droplets are formed from the fluid containing the microparticles. In other words, "delay time" refers to the necessary time from the time that the microparticles are detected by the detection unit 3 to when the droplets containing the microparticles have a charge applied thereto by the charge unit 11. In the present technology, the term "delay time" refers to the duration of from the time at which the microparticles are detected by the detection unit 3, to the time at which the intensity within the image region, which is set automatically, in the image information imaged by the droplet camera 4 described below reaches a maximum.

1-2 Microchip

FIGS. 2A and 2B and FIGS. 3A to 3C show an example of the microchip 2 which may be installed in the flow cytometer 1.

Figure 2A:
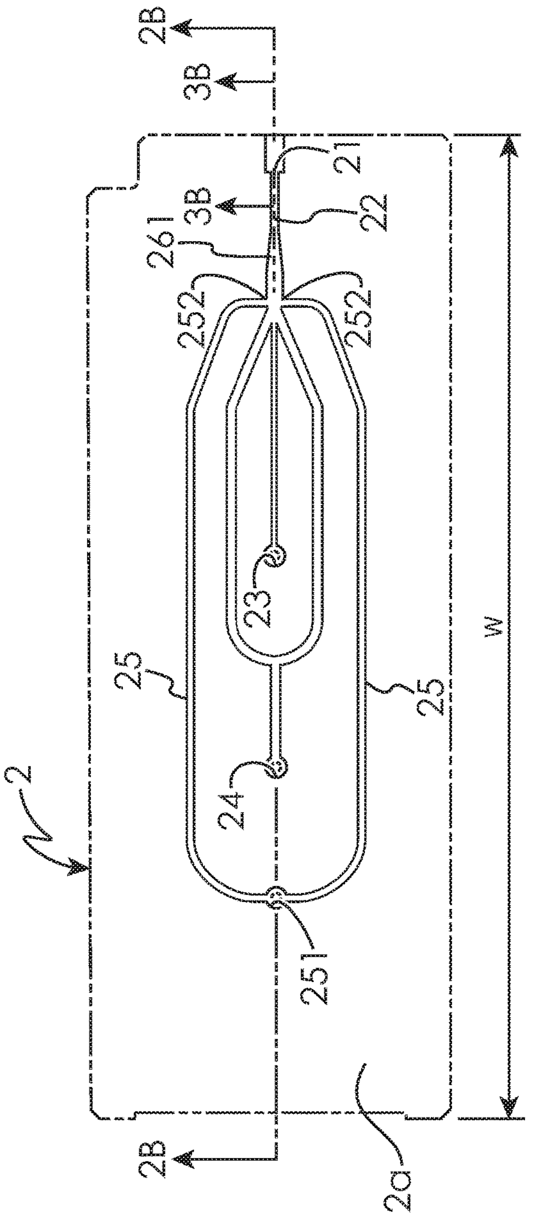
FIGS. 2A and 2B are schematic views for illustrating an example of a microchip which may be installed in the flow cytometer.
Figure 2B:
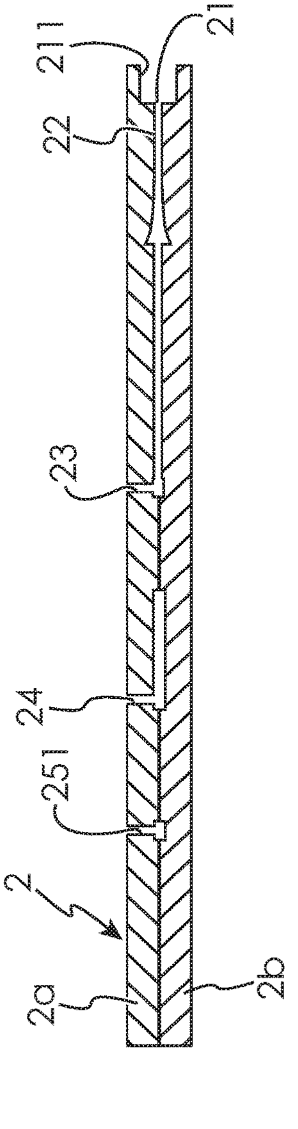
Figure 3A:
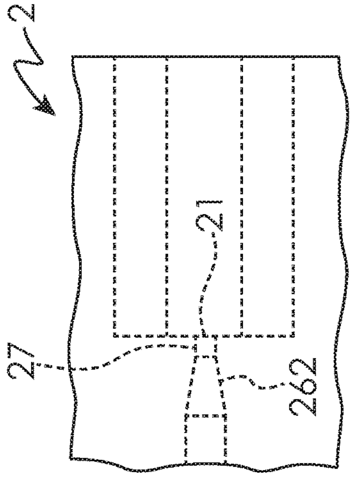
FIGS. 3A to 3C are schematic views for illustrating the configuration of an orifice of the microchip.
Figure 3B:
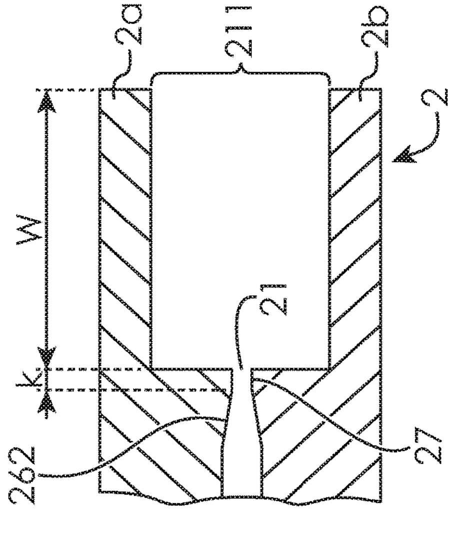
Figure 3C:
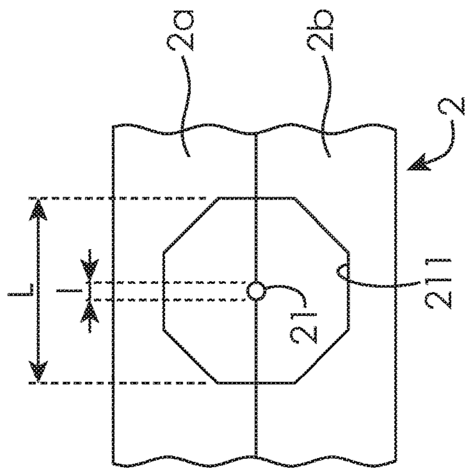

FIG. 2A shows a schematic view of the upper surface, and FIG. 2B shows a cross-sectional schematic view corresponding to the line IIB-IIB in FIG. 2A. In addition, FIGS. 3A to 3C schematically illustrate the configuration of the orifice 21 of the microchip 2, FIG. 3A shows an upper surface schematic view, FIG. 3B shows a cross-section schematic view, and FIG. 3C shows a front surface schematic view. FIG. 3B corresponds to the cross section along the line IIIB-IIIB in FIG. 2A.

The microchip 2 is formed of substrate layers 2*a* and 2*b* which are bonded together to form a sample flow path 22. It is possible to perform the formation of the sample flow path 22 from the substrate layers 2*a* and 2*b* through injection molding of a thermoplastic resin using a metal mold. For the thermoplastic resin, plastics generally used in the related art as microchip materials such as polycarbonate, polymethyl methacrylate resin (PMMA), cyclic polyolefin, polyethylene, polystyrene, polypropylene and polymethyl disilazane (PDMS) may be adopted.

The sample fluid is introduced to the sample inlet 23 from the fluid delivery connector portion, merges with the sheath fluid which is introduced from the fluid delivery connector portion to a sheath inlet 24, and is delivered through the sample flow path 22. The sheath fluid introduced from the sheath inlet 24, after being split into two directions and delivered, in the merging portion in which the sheath fluid merges with the sample fluid introduced from the sample inlet 23, the sheath fluid merges with the sample fluid so as to interpose the sample fluid from two directions. Therefore, in the merging portion, in the center of the sheath fluid laminar flow, a three-dimensional laminar flow in which the sample laminar flow is positioned is formed.

Reference numeral 25 represents a suction flow path for applying a negative pressure to the sample flow path 22 when clogging or bubbles occur in the sample flow path 22, which temporarily causes the flow to flow backward in order to resolve the clogging or bubbles. On one end of a suction flow path 25, a suction outlet 251 connected to a negative pressure source such as a vacuum pump via the liquid delivery connector portion is formed, and the other end is connected to the sample flow path 22 in a communication hole 252.

In the three-dimensional laminar flow, the laminar flow width is limited in a limiter portion 261 (refer to FIGS. 2A and 2B) and 262 (refer to FIGS. 3A to 3C) formed such that the surface area of the vertical cross section thereof in relation to the fluid delivery direction gets smaller gradually or in stages from upstream in the fluid delivery direction to downstream. After this, the three-dimensional laminar flow becomes a fluid stream (refer to FIG. 1) from the orifice 21 provided on one side of the flow path, and is discharged. In FIG. 1, the discharge direction of the fluid stream from the orifice 21 is represented by the Y axis positive direction.

The connection portion to the orifice 21 of the sample flow path 22 is a straight portion 27, which is formed linearly. The straight portion 27 functions such that the fluid stream from the orifice 21 is ejected in a straight line in the Y axis positive direction.

The fluid stream ejected from the orifice 21 is transformed into droplets by the oscillation applied to the orifice 21 by a chip excitation unit. The orifice 21 is open in the end face direction of the substrate layers 2*a* and 2*b*, and a notch portion 211 is provided between the opening position thereof and the substrate layer end face. The notch portion 211 is formed by notching the substrate layers 2*a* and 2*b* between the opening portion of the orifice 21 and the substrate end face such that the diameter L of the notch portion 211 is larger than the opening diameter 1 of the orifice 21 (refer to FIG. 3C). It is desirable to form the diameter L of the notch portion 211 two times or larger than the opening diameter 1 of the orifice 21 so as not to obstruct the movement of the droplets discharged from the orifice 21.

1-3 Detection Unit

The reference numeral 3 in FIG. 1 represents the detection unit which detects the measurement target light emitted from the microparticles such as cells through the irradiation of a laser L1 emitted from a light source 31. The detection unit 3 performs characteristic detection of the cells between the limiter portion 261 (refer to FIGS. 2A and 2B) and the limiter portion 262 (refer to FIGS. 3A to 3C) of the sample flow path 22. The characteristic detection is not particularly limited, however, for example, in a case in which optical detection is used, the scattered light and the fluorescent light emitted from the cells due to the irradiation of laser L1 (refer to FIG. 1) in relation to the cells which are fluid delivered arranged in a single row in the sample flow path 22 in the center of the three-dimensional laminar flow, are detected by the detection unit 3.

For the irradiation and detection of the light, in addition to the laser light source, irradiation systems that condense and irradiate a laser onto the cells such as a condensing lens, a dichroic mirror or a band pass filter may also be configured. The detection system is, for example, configured by an area imaging device such as a PMT (photo multiplier tube), or a CCD or CMOS device.

The measurement target light detected by the detection system of the detection unit 3 is light emitted from the cells due to the irradiation of the measurement light, and for example, may be scattered light, fluorescent light or the like such as forward scattered light, side scattered light, Rayleigh scattering, or Mie scattering. These measurement target lights are converted into an electrical signal, output to a control unit 7, and utilized in the optical characteristic discrimination of the cells.

Furthermore, the detection unit 3 may also detect the characteristics of the cells magnetically or electrically. In this case, microelectrodes are disposed opposing one another in the sample flow path 22 of the microchip 2, and the resistance value, the capacitance value, the inductance value, the impedance, the change value of the electric field between the electrodes, or the magnetization, the change in the magnetic field, or the like are measured.

1-4 Droplet Camera

The reference numeral 4 in FIG. 1 represents an example of the imaging device of the present technology, which is a droplet camera for imaging the droplet D discharged from the orifice 21 of the microchip 2 such as a CCD camera, a CMOS sensor, or the like. The droplet camera 4 is designed such that it is possible to perform focus adjustment of the image of the droplet D which is imaged. In the flow cytometer 1, the droplets near the break-off point are imaged by strobe L2 emitted from the light source 41. The strobe L2 may include a plurality of different types of strobes from multiple light sources 41. For example, one strobe L2 may include an LED strobe, which provides sufficient light to obtain a droplet image of the droplets at and near the break-off point. Additionally, another strobe L2 may include a calibration strobe, which excites the microparticles within the droplets. The excitation of the microparticles provided by the calibration strobe allows the droplet camera to obtain a calibration image, which shows the location of the microparticles and is used to determine their sum of intensity, as described below. Generally, the LED strobe is much shorter than the calibration strobe because the emission from the microparticles due to the calibration strobe is dim, and therefore a longer calibration strobe is needed to get a quality calibration image. For example, the LED strobe length may be about 2% of the droplet clock cycle whereas the calibration strobe may be about 50% of the droplet clock cycle.

In addition, in the flow cytometer 1, due to the microchip being exchanged for a new microchip, or the external environment (the temperature and the like) changing, there are cases in which it is necessary to change the droplet formation parameters (sheath pressure, droplet frequency, piezo drive pressure, and the like). In this case, it is necessary to adjust the time until the charge is applied to the droplets containing the microparticles after the microparticles are detected by the detection unit 3 (hereinafter, this time is also referred to as the delay time). The droplet camera 4 functions in order to image the droplet D, and also in order to make it possible for the control unit 7 described below to determine the delay time.

More specifically, the droplet camera 4 is designed such that it is possible to image a plurality of images of the droplet D at a plurality of different times such that the control unit 7 described below may determine the delay time. Furthermore, the term "delay time" refers to the duration from the time at which the microparticles are detected by the detection unit 3, to the time at which the intensity within the image region, which is calculated by comparing a plurality of items of image information of the droplets imaged by the droplet camera 4, reaches a maximum. In addition, the term "plurality of different times", for example, refers to each time, the interval between which is the time of the reciprocal of the frequency of the oscillation which an oscillating element 13 applies to the orifice 21 (in other words, the discharge interval time of each of the droplets D).

In addition, in order for the control unit 7 to be able to determine the delay time, the droplet camera 4 is designed to be able to image a plurality of images of the droplet D within a predetermined time after the delay time has elapsed from the time at which the microparticles are detected by the detection unit 3. Furthermore, the term "predetermined time" refers to a time shorter than the discharge interval time of each of the droplets D.

In addition, the droplet camera 4 is designed to be movable in the positive direction or the negative direction along the Y axis such that the control unit 7 may determine the optimal discharge frequency of the droplets D described below.

In addition, the images imaged by the droplet camera 4 are displayed on the display unit such as a display, and are also used to allow the user to confirm the formation state of the droplet D (the size, shape, interval, and the like of the droplet) in the orifice 21.

1-5 Deflection Plate

The reference numerals 51 and 52 in FIG. 1 represent a pair of deflection plates which are disposed opposite one another to interpose the droplet D which is ejected from the orifice 21 and imaged by the droplet camera 4.

Deflection plates 51 and 52 are configured to contain the electrodes which control the movement direction of the droplets discharged from the orifice 21 using the electrical force on the charge applied to the droplets. In addition, the deflection plates 51 and 52 also control the trajectory of the droplet D emitted from the orifice 21 using the electrical force on the charge applied to the droplet D. In FIG. 1, the opposing direction of the deflection plates 51 and 52 is represented by the X axis direction.

1-6 Collection Container

In the flow cytometer 1, the droplet D is accepted by one of the plurality of collection containers 611, 612, 62, or 63 which are disposed in a row in the opposing direction of the deflection plates 51 and 52 (the X axis direction). The collection containers 611, 612, 62, or 63 may also be plastic tubes or glass tubes which are normally used for experiments. The number of the collection containers 611, 612, 62, or 63 is not particularly limited, however, here, a case in which four are disposed is illustrated. The droplet D emitted from the orifice 21 is guided into and collected in one of the four collection containers 611, 612, 62, or 63 according to the presence or absence, or alternatively the magnitude of the electrical force between the deflection plates 51 and 52.

The collection containers 611, 612, 62, and 63 are disposed in a container for use as the collection container (not shown) in an exchangeable manner. The container for use as the collection container (not shown) is disposed on the Z axis stage (not shown) configured to be movable in the direction (the Z axis direction) orthogonal to the discharge direction (the Y axis direction) of the droplet D from the orifice 21 and to the opposing direction (X axis direction) of the deflection plates 51 and 52.

1-7 Control Unit or Similar

The flow cytometer 1, in addition to the configuration described above, is provided with a data analysis unit for characteristic discrimination of the cells or the like detected by the detection unit 3, a tank portion for retaining the sample fluid and the sheath fluid, the control unit 7 for controlling each of the configurations described above, and the like which an ordinary flow cytometer is provided with.

The control unit 7 may be configured by an ordinary computer provided with a CPU, memory, a hard disk and the like, and on the hard disk is stored the OS, a program to execute each step relating to the delay time determination method described next, and the like.

2. Delay Time Determination Method in Microparticle Sorting Apparatus according to Present Technology 2-1 Microparticle Detection Step S1

Figure 4:
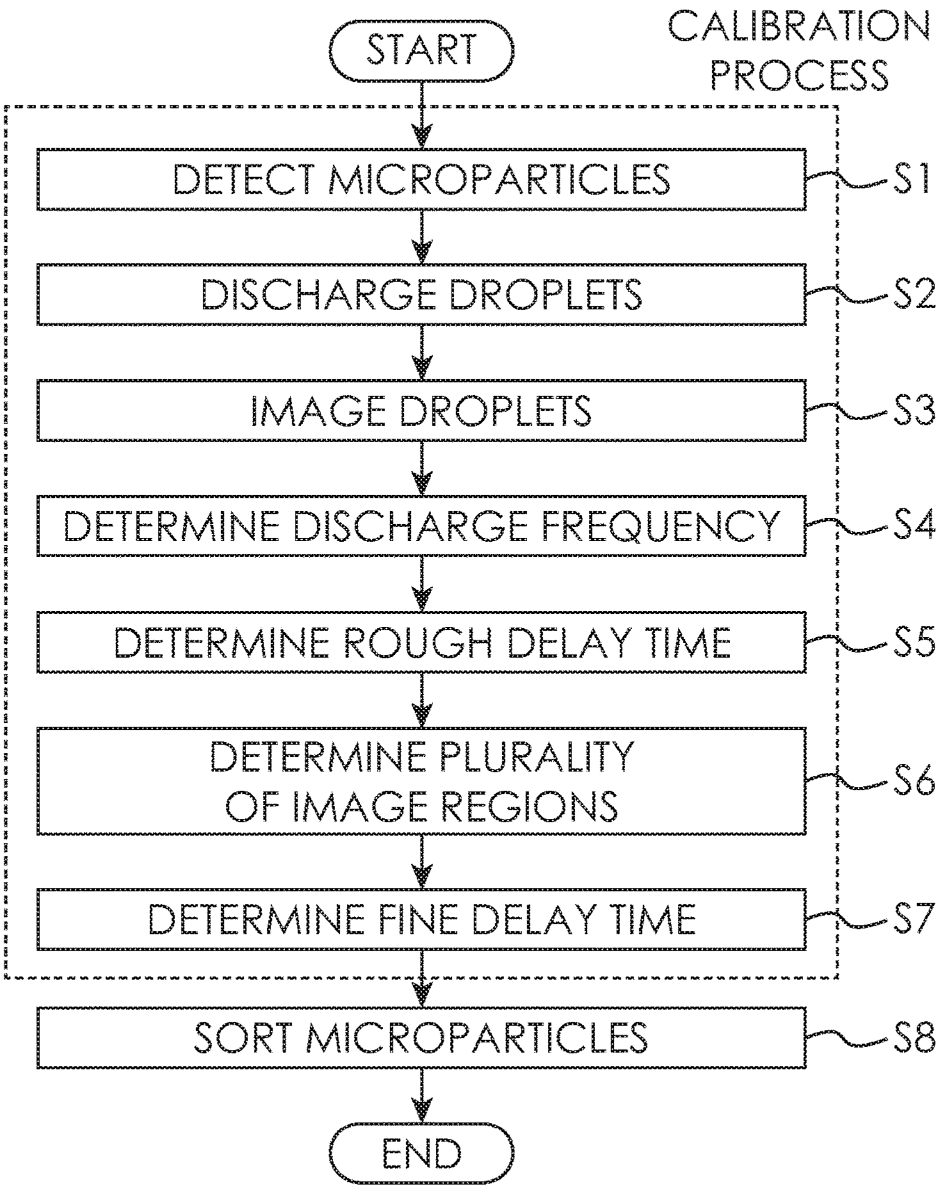
FIG. 4 is a flow diagram for illustrating the method of determining the delay time in the flow cytometer.

FIG. 4 is flow chart for illustrating the delay time determination step in the flow cytometer 1. The delay time determination step includes the processes of "microparticle detection step S1", "droplet discharge step S2", "droplet imaging step S3", "discharge frequency determination step S4", "image region determination step S5", and "delay time determination step S6". In addition, a process of "microparticle sorting step S7" may also be executed after the delay time determination steps described above. Description will be given of each process below.

First, in the microparticle detection step S1, the control unit 7 outputs a signal to the fluid delivery connector portion and begins fluid delivery of the sample fluid and the sheath fluid. Furthermore, the detection unit 3 detects the microparticles contained in the sample at the sample flow path 22 by, for example, the irradiation of the laser L1. Furthermore, the present step S and the steps S2 to S6 described below are a calibration process for determining the delay time from when the detection unit 3 detects the target cells or the like until the charge unit 11 applies a charge to the droplets containing the cells or the like. Therefore, it is preferable to use calibration beads such as particles for industrial use, the shape and the like of which is clear, beforehand as the microparticles.

2-2 Droplet Discharge Step S2

In the droplet discharge step S2, the oscillating element 13 applies an oscillation to the orifice 21, the droplet D is discharged from the orifice 21, the droplets D is collected in the waste fluid inlet, and it is possible to dispose of the fluid (refer to FIG. 4).

2-3 Droplet Imaging Step S3

In droplet imaging S3, the control unit 7 outputs a signal to the droplet camera 4, and the droplet camera 4 that received the signal images the droplet D which is discharged and strobed by the strobe L2 (refer to FIG. 4). The droplet camera 4 may image the images at an interval that is the same as or shorter than the interval of the droplet clock described below.

Figures 5A, 5B, 5C, 5D:
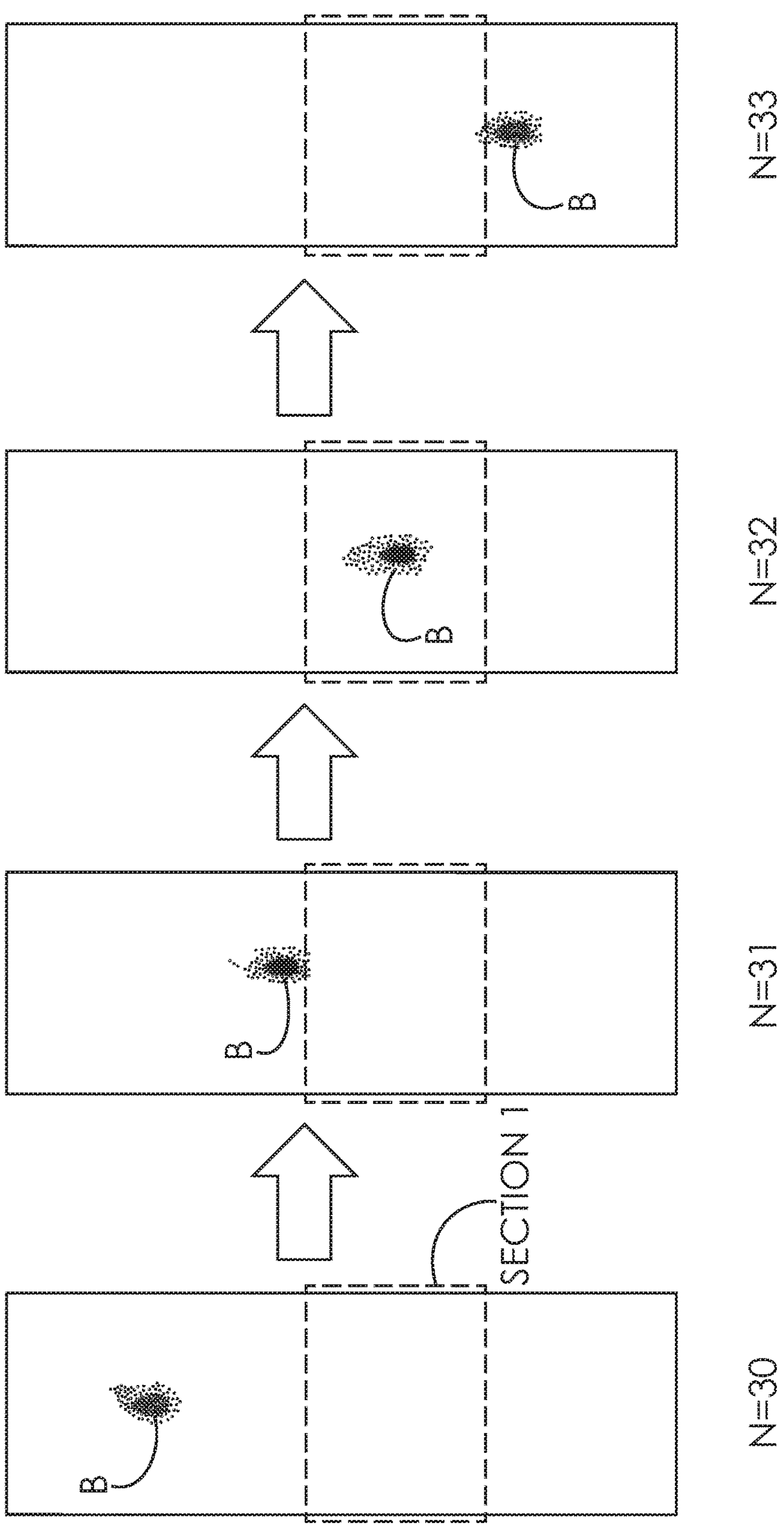
FIGS. 5A to 5D are explanatory diagrams, which are examples of images of a droplet imaged by a droplet camera of the flow cytometer, for illustrating the rough delay time determination step.
Figure 6A:
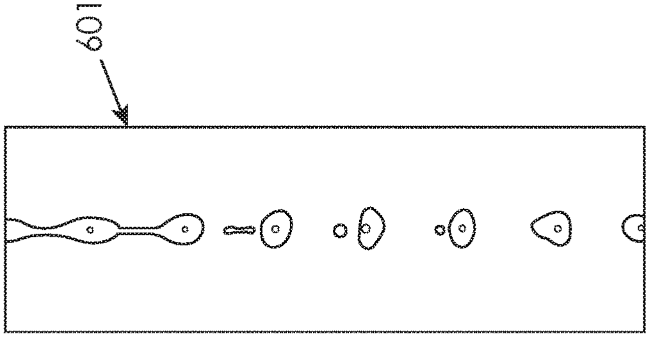
FIGS. 6A to 6C are explanatory diagrams, where
Figure 6B:
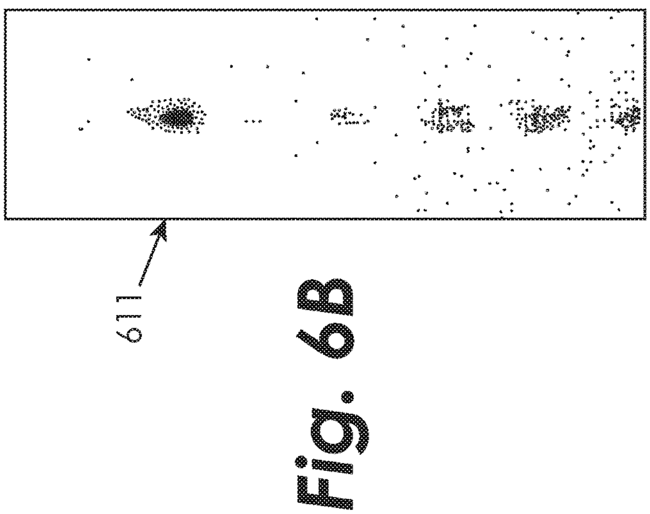
Figure 6C:
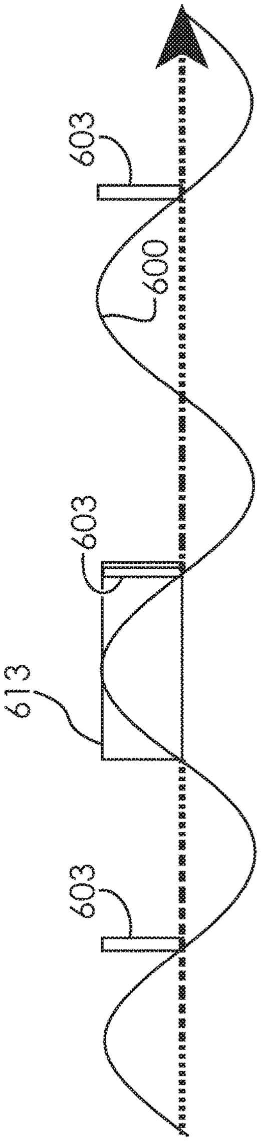

Referring to FIGS. 5A-5C, the droplet camera 4 may image a droplet image 501 and a calibration image 511. To obtain the droplet image 501, depicted in FIG. 5A, an LED strobe 503 is emitted as strobe L2. To obtain the calibration image 511, depicted in FIG. 5B, a calibration strobe 513, which excites the microparticles, is emitted from strobe L2. As described above, the LED strobe 503 is generally shorter than the calibration strobe 513. FIG. 5C depicts an exemplary embodiment of the difference in timing between the LED strobe 503 and the calibration strobe 513, in relation to the droplet clock 500.

At this time, for example, the control unit 7 may output a signal to the droplet camera 4 and make the droplet camera 4 that received the signal move in the X axis direction or the Y axis direction. Furthermore, the control unit may perform focus adjustment in the Z axis direction in the imaging of the images of the droplet D by the droplet camera 4. For example, the control unit 7 may perform focus adjustment until the contrast ratio in the image imaged by the droplet camera 4 falls within a predetermined range.

2-4 Discharge Frequency Determination Step S4

In the discharge frequency determination step S4, the control unit 7 moves the droplet camera 4 to a predetermined position and adjusts the discharge frequency of the droplets D based on the image information imaged by the droplet camera 4 (refer to FIG. 4). The predetermined position described above is not particularly limited, however, it may be a position set beforehand according to the discharge conditions such as the orifice diameter and the drive pressure.

Furthermore, the control unit 7 determines the optimal discharge frequency of the droplets D to be the discharge frequency at which the position where the droplets D start forming in the Y axis direction (hereinafter referred to as the break-off point) is closest to the orifice 21. Furthermore, the present step S4 may also be executed after the step S5 described below.

In this manner, in the flow cytometer 1, since the optimal discharge frequency is determined by the control unit 7 based on the break-off point, it is possible to resolve the complication of the user setting the droplet frequency manually.

2-5 Rough Delay Time Determination Step

In the rough delay time determination step S5, the control unit 7 determines the rough delay time of the droplet D by comparing the plurality of items of image information of the droplet D imaged by the droplet camera 4 from the time at which the microparticles are detected by the detection unit 3 (refer to FIG. 4).

The term "rough delay time" here refers to the time which is provisionally treated as the delay time by the present step S5, which is the period until the fine delay time is determined by the delay time step S7 described below. More specifically, the term "rough delay time" refers to the duration of from the time at which the microparticles are detected by the detection unit 3, to the time at which the sum of intensity of calibration image(s) taken at a plurality of different times of a droplet reaches a maximum in a predetermined region (described below). Alternatively, this can be determined by when a number of bright spots within the predetermined region, which is calculated by comparing a plurality of calibration images of the droplet D imaged by the droplet camera 4 at a plurality of different times, reaches a maximum. Furthermore, the term "plurality of different times" is not particularly limited, however, for example, refers to each time, the interval between which is the time of the reciprocal of the frequency of the oscillation which the oscillating element 13 applies to the orifice 21 (in other words, refers to the discharge interval time of each of the droplets D, and is referred to as the "droplet clock" hereinafter).

FIGS. 5A to 5D are photographs showing examples of images of a droplet imaged by the droplet camera 4 of the flow cytometer 1, and represent the images which are imaged at different times (refer to FIGS. 5A to 5D). More specifically, FIGS. 5A to 5D are photographic views for illustrating which of the droplets the detected microparticles are contained in when the droplet D imaged by the droplet camera 4 at the time (T0) at which the microparticle is detected by the detection unit 3 is set as the first droplet. Furthermore, each photographic view may also be a view in which a plurality of imaged images are integrated together.

In FIGS. 5A to 5D, the term "Section 1" refers to the predetermined region set beforehand in the image P.

The control unit 7 compares the plurality of images of the droplet D imaged by the droplet camera 4 at the interval of the droplet clock, and preliminarily determines the time from T0 until when the number of the sum of intensity (or the number of bright spots) in "Section 1" reaches a maximum as the rough delay time. Furthermore, the term "sum of intensity" will be discussed in further detail below. Additionally, "bright spot" refers to pixels which have a higher brightness than a predetermined threshold in the image of the droplet D imaged by the droplet camera 4, and is an item of image information of the microparticles contained in the excited droplet D, irradiated by the laser L2.

In FIGS. 5A to 5D, as an example of the present technology, the term "bright spot" refers to the images which are imaged by the droplet camera 4 when the 30th to 33rd droplets are discharged, when the droplet D discharged from the orifice 21 at T0 and imaged by the droplet camera 4 is set as the first droplet. For example, the 30th droplet is the photographic view represented by N=30 (refer to FIG. 5A).

In the example shown in FIGS. 5A to 5D, the control unit 7 can discriminate that the microparticles are contained in the 32nd droplet based on the image information of N=32 (refer to FIG. 5C) in which the number of bright spots B within "Section 1" reaches a maximum. In other words, the control unit 7 compares the plurality of images of the droplet D imaged by the droplet camera 4 at the interval of the droplet clock, and can preliminarily determine the rough delay time from the time that the microparticles are detected until the time that the 32nd droplet is discharged as the rough delay time.

In this manner, in the flow cytometer 1, it is possible to preliminarily determine the rough delay time as the delay time by comparing the sum of intensity (or the number of bright spots) in the image information within "Section 1" in relation to a plurality of different times.

2-6 Image Region Determination Step S6

In the image region determination step S6, the control unit 7 determines the plurality of image regions by analyzing the image information of the droplet D imaged by the droplet camera 4. In one embodiment, the control unit 7 determines the plurality of image regions by analyzing the droplet images 601 imaged by the droplet camera 4.

The term "plurality of image regions" here refers to the regions of the droplet image 601 of which the intensity will be measured and drop delay determined, as described below, which is calculated by comparing a plurality of items of image and where the intensity information of the droplet D imaged by the droplet camera 4 at a plurality of different times, reaches a maximum. Furthermore, the term "plurality of different times" is not particularly limited, however, for example, refers to each time, the interval between which is the time of the reciprocal of the frequency of the oscillation which the oscillating element 13 applies to the orifice 21 (in other words, refers to the discharge interval time of each of the droplets D, and is referred to as the "droplet clock" hereinafter).

Figures 7A, 7B, 7C:
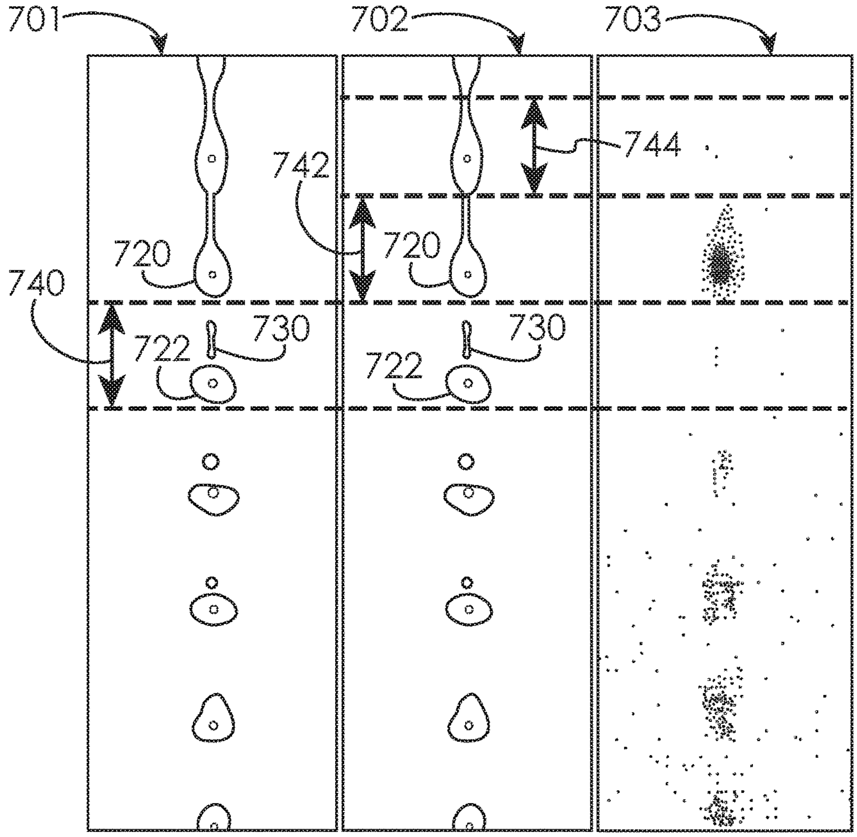
FIGS. 7A to 7D are exemplary images for illustrating the first method of determining a plurality of image regions, where
Figure 7D:
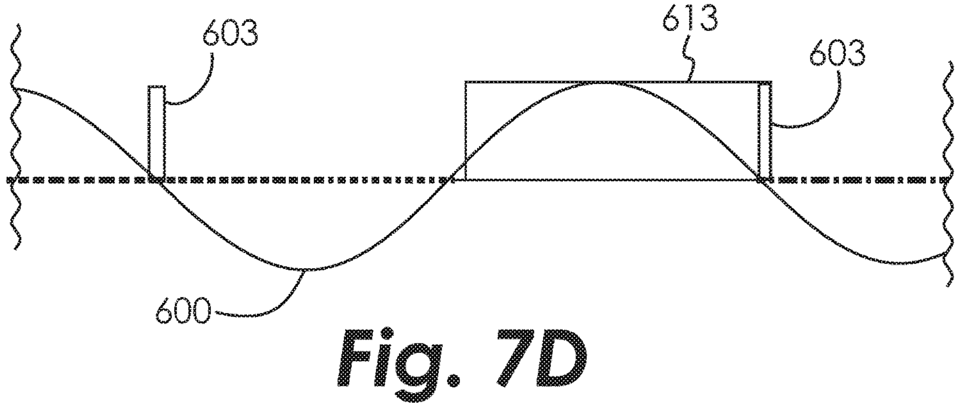

There are two methods of determining the plurality of image regions. The first method involves detecting the lower edge of droplets D and the second method involves detecting the upper edge of droplets D. More particularly, in the first method, the lower edge of the last attached droplet and the lower edge of the first detached droplet are detected. FIGS. 7A to 7C are photographs showing examples of the droplet images 701, 702 (FIGS. 7A and 7B) and calibration image 711 (FIG. 7C) at a given time and represent the process of determining the plurality of image regions according to the first method. More specifically, in FIG. 7A, the lower edge of the last attached droplet 720 and the lower edge of the first detached droplet 722 are shown. The region defined by the distance between the lower edge of the last attached droplet 720 and the lower edge of the first detached droplet 722 is a lowest image region S2, which is one of the plurality of image regions. This distance between the lower edge of the last attached droplet 720 and the lower edge of the first detached droplet 722 may be generally referred to as the image region height, or, in this specific case, the S2 image region height 740. In one embodiment, the other image regions are determined as follows. The S2 image region height 740 is measured, and the same distance is applied to create two more image regions, S1 and S0, directly above the lowest image region S2. Preferably, the middle image region is labeled S1 (having an S1 image region height 742) and the uppermost image region is labeled S0 (having an S0 image region height 744). Therefore, each image region S0, S1, S2 has the same image region height 740, 742, 744. FIG. 7B shows a droplet image 702 with the three image regions S0, S1, S2 depicted and FIG. 7C depicts the calibration image 611 of FIG. 7B, also with the three image regions S0, S1, S2 depicted. In another embodiment, after the S2 image region height is determined (as discussed above) the S1 image region height and the S2 image region height are each determined individually by determining the lower edge for each of two attached droplets above the last attached droplet 720. Therefore, in this embodiment, the S2, S1, and S0 image region heights 740, 742, and 744 do not necessarily occupy the same distance. Although described as two separate embodiments for determining the image region heights, they may be used in combination. For example, the S2 and S1 image region heights 740, 742 may each be individually through the method described in the second embodiment whereas the S0 image region is determined by duplicating the image region height of either the S2 and S1 image region heights 740, 742. This first method of determining the plurality of image regions is preferential when the droplet stream includes a fast satellite. A fast satellite is when the satellite 730 eventually combines with the droplet before the satellite 730 (i.e., the droplet below the satellite in FIGS. 7A and 7B). Determining the plurality of image regions using this method includes the satellite 730 in the image region with the droplet with which it will eventually combine. In addition, FIG. 7D depicts one embodiment of the LED strobe 603 and calibration strobe 613 in relation to the droplet clock 600 for the first method. As shown in FIG. 7D, the calibration strobe 613 and LED strobe 603 in this exemplary embodiment end at the same time, with the LED 603 strobe being shorter than the calibration strobe 613.

Figures 8A, 8B, 8C:
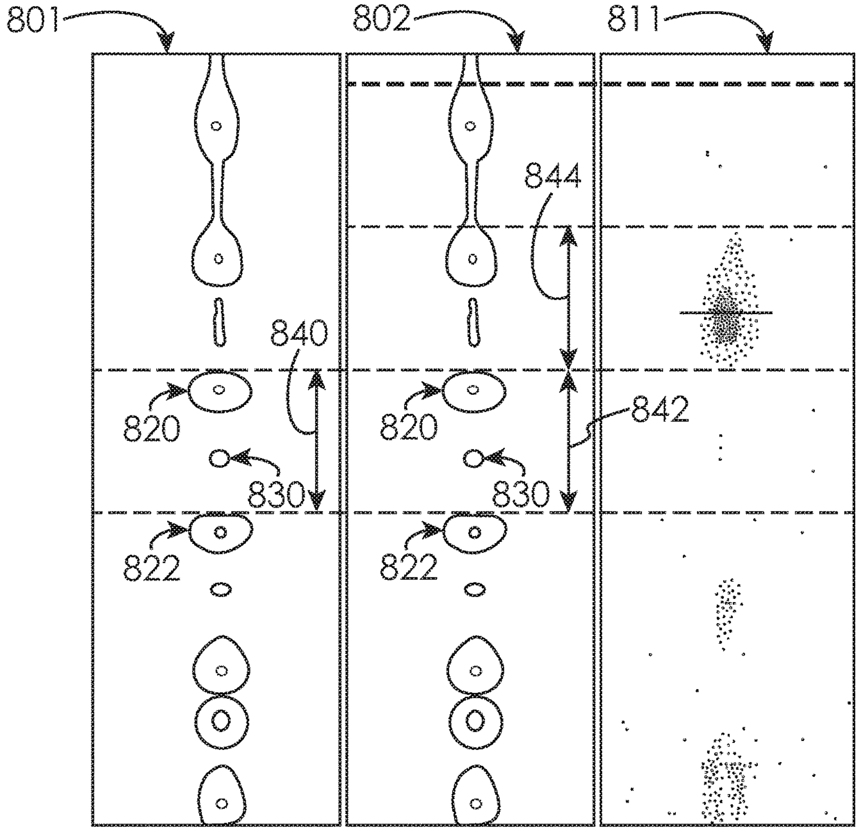
FIGS. 8A to 8D are exemplary imaged for illustrating the second method of determining a plurality of image regions, where
Figure 8D:
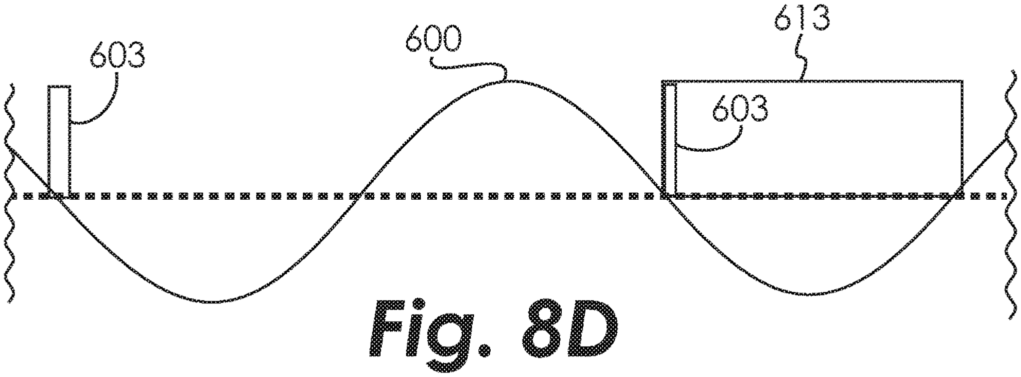

FIGS. 8A to 8C depict the second method of determining the plurality of image regions. Particularly, in the second method of determining the plurality of image regions, the upper edge of the first detached droplet 820 and the second detached droplet 822 are detected. In FIG. 8A, the upper edge of the first and second detached droplets 820, 822 are shown. The region defined by the distance between the upper edge of the second detached droplet 822 and the upper edge of the first detached droplet 822 is a lowest image region S2, which is one of the plurality of image regions. This distance between the upper edge of the second detached droplet 822 and the upper edge of the first detached droplet 822 may be generally referred to as the image region height, or, in this specific case, the S2 image region height 840. In one embodiment, the other image regions are determined as follows. The S2 image region height 840 is measured, and the same distance is applied to create two more image regions, S1 and S0, directly above the lowest image region S2. Preferably, the middle image region is labeled S1 (having an S1 image region height 842) and the uppermost image region is labeled S0 (having an S0 image region height 844). Therefore, each image region S0, S1, S2 has the same image region height 840, 842, 844. FIG. 8B shows a droplet image 802 with the three image regions S0, S1, S2 depicted and FIG. 8C depicts the calibration image 811 of FIG. 8B, also with the three image regions S0, S1, S2 depicted. In another embodiment, after the S2 image region height 840 is determined (as discussed above) the S1 image region height 842 and the S2 image region height 844 are each determined individually by determining the upper edge of the last attached droplet and the upper edge of the droplet above the last attached droplet. Therefore, in this embodiment, the S2, S1, and S0 image region heights 840, 842, and 844 do not necessarily have the same distance. Although described as two separate embodiments for determining the image region heights, they may be used in combination. For example, the S2 and S1 image region heights 840, 842 may each be individually through the method described in the second embodiment whereas the S0 image region is determined by duplicating the image region height of either the S2 and S1 image region heights 840, 842 through the method described in the first embodiment. The second method of determining the plurality of image regions is preferential when the droplet stream includes a slow satellite. A slow satellite is when the satellite eventually combines with the droplet after the satellite (i.e., the droplet above the satellite in FIGS. 8A and 8B). Determining the plurality of image regions using this method includes the satellite 830 in the image region with the droplet with which it will eventually combine. In addition, FIG. 8D depicts one embodiment of the LED strobe 603 and calibration strobe 613 in relation to the droplet clock 600 for the second method. As shown in FIG. 7D, the calibration strobe 613 and LED strobe 603 in this exemplary embodiment begin at the same time, with the LED strobe 603 being shorter than the calibration strobe 613.

2-7 Fine Delay Time Determination Step

In the delay time determination step S7 shown in FIG. 4, first, the control unit 7 refers to the adjacent information described above based on the plurality of image regions of the droplet D imaged by the droplet camera 4. The method is described below with reference to FIG. 8 to FIG. 10. Furthermore, the adjacent information is information related to the sum of intensity in the plurality of image regions.

2-7-0 General Fine Delay Time Determination Steps

First, the background intensity of the calibration images is determined by obtaining an image where neither the LED strobe nor the calibration laser is excited. In essence, the background intensity is an image with no light source but for any background light that may be present.

Second, the calibration images of the droplets are taken and accumulated at a pre-set delay time. A plurality of calibration images are taken by the camera. When the fluorescence of the beads within the droplets is weak, the plurality of droplet images may be aggregated to obtain a final calibration image. Any number of calibration images may be aggregated to obtain the final calibration image. The aggregation of calibration images assists in obtaining a calibration image to be measured that has brighter spots.

Third, the background intensity is subtracted from the calibration image (whether it be a single calibration image or an aggregate of multiple calibration images). Either a single background sum of intensity can be subtracted, or the background sum of intensity multiplied by the number of calibration images aggregated can be subtracted.

Fourth, after the calibration image is obtained (whether it be a single calibration or an aggregate of multiple calibration images) the sum of intensity of each of the image regions is determined. In this process, each image region is broken down into a plurality of image region sub-areas. For example, the image region may contain sub-areas defined by each pixel in the calibration image. Preferably, the sub-areas are rectangular in shape (e.g., a square), however any other geometric shape with three or more sides is appropriate. Similarly, the sub-areas may all have the same area, however, the present method is not limited to methods where the sub-areas all have the same area. Once each sub area is set, each individual sub-area's intensity is determined. For example, the sub-area may have an intensity range from 0 to 255 when a camera is being used that allows for 8 bits of data per pixel. Alternatively, a camera that allows 10 bits of data per pixel would have an intensity range of 0 to 1024. The intensity is measured based on the calibration image. Once each individual sub-area's intensity is determined, the sum of intensities of all sub-areas within an image region is determined by summing the individual sub-area intensities. This process is repeated for each image region such that each image region has its own sum of intensity value. This sum of intensity value for each image region (S0, S1, and S2) is plotted on a graph.

Figure 9:
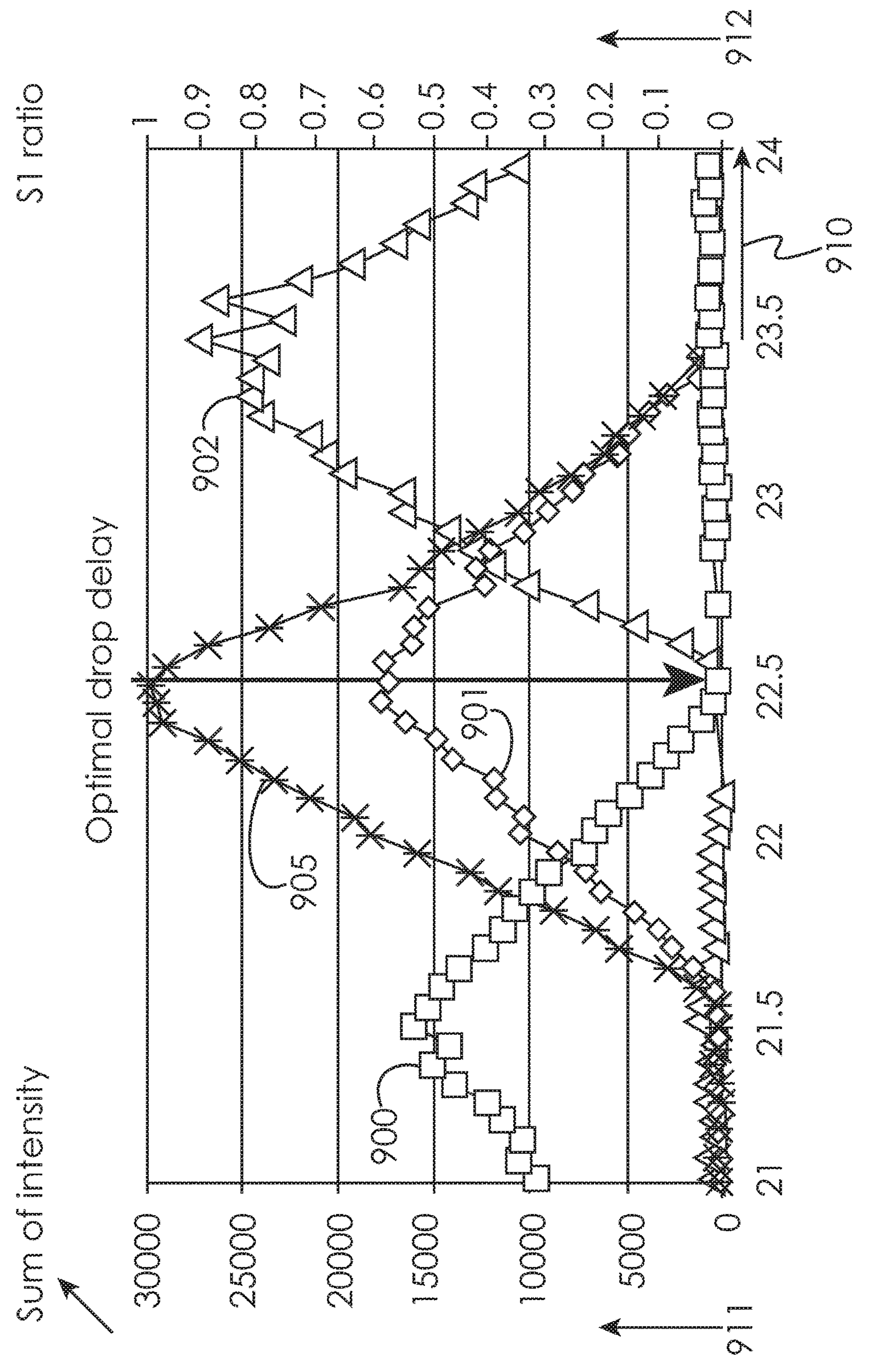
FIG. 9 is an explanatory diagram, which is a graph in which the horizontal axis is the delay time, the vertical axis on the left is the sum of intensity of the images of the droplets imaged by the droplet camera of the flow cytometer, and the vertical axis on the right is the S1 ratio, for illustrating an example of the delay time determination step (the first delay time determination method)
Figure 10:
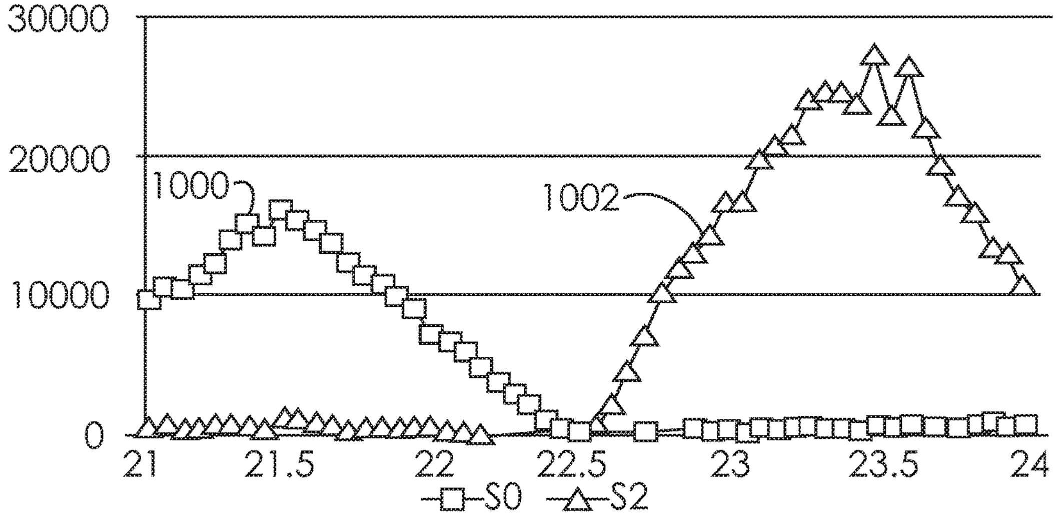
FIG. 10 is an explanatory diagram, which is a graph in which the horizontal axis is the delay time and the vertical axis is the sum of intensity of the images of the droplets imaged by the droplet camera of the flow cytometer, for illustrating an example of the delay time determination step (the second delay time determination method)

Fifth, a new delay time is selected, and the second through fourth steps of the preceding paragraphs are repeated. This step itself is then repeated until the sum of intensity value for each of the image regions is determined for two or more delay times. In one embodiment, the two or more delay times for which the sum of intensities are determined spans a plurality of delay time values. For example, the two or more delay times span a total of three or five full delay time periods. In another embodiment, the two or more delay times for which the sums of intensity are determined are at equivalent intervals. For example, when a delay time period is 360 degrees, each delay time for which sums of intensity are determined are separated by 20 degrees. In this instance 55 total delay times for which sums of intensity are determined will occur when done so for a period of three full delay times (e.g., delay times: 30, 30+20°, 30+40°, . . . , 33). In an alternative embodiment, the delay times for which sums of intensity are determined are separated by 40 degrees, 60 degrees, or 90 degrees. At each delay time for which sums of intensity are determined, the sum of intensity for S0, S1, and S2 is plotted on a graph. Examples of such graphs are depicted in FIGS. 8-10 (discussed in detail below). For methods where three full delay time periods are to be plotted, the first delay time for which sums of intensity are determined may be at one full delay time period less than the rough delay time determined above. For example, if the rough delay time is 30, then this repetitive process would start at delay time 29 and continue to measure the sums of intensity of the image regions at each successive interval (i.e., when 20 degree intervals are selected: delay time 29, 29+20°, 29+40°, . . . , 32). However, you may also start at two delay times less than the rough delay time and proceed for three delay periods (i.e., to one delay time greater than the rough delay time). Any range around the rough delay time is acceptable, so long as the rough delay time is included within that range.

Finally, each of the sums of intensity for each image region is determined and plotted on a graph (as discussed above) the fine delay time is determined using one of the methods below.

2-7-1 First Fine Delay Time Determination Method

First, description will be given of the first delay time determination method with reference to FIG. 9, in which the delay time is determined by referring to the sum of intensity of all three image regions S0, S1, S2.

FIG. 9 is a graphical representation of the sum of intensity measurements for each image region S0, S1, S2, over a span of three drop delay times. The x-axis represents the drop delay time 910, the y-axis on the left represents the sum of intensity 911, and the y-axis on the right represents the S1 ratio 912 (described below). In FIG. 9, the line 900 represents the sum of intensity at various drop delay times for region S0, the line 901 represents the sum of intensity at various drop delay times for region S1, the line 902 represents the sum of intensity at various drop delay times for region S2, the line 905 represents the S1 ratio (described below).

Then, the S1 ratio is determined. The S1 ratio is determined using the following equation:

$$S1\ \text{Ratio} = \left(\frac{S1}{S0 + S1 + S2}\right)$$

In the S1 Ratio equation, S1 represents the sum of intensity of image region S1 at a given drop delay time, S2 represents the sum of intensity of image region S2 at a given drop delay time, and S0 represents the sum of intensity of image region S0 at a given drop delay time. The S1 Ratio is measured for each drop delay time where a sum of intensity is measured in the above step, and the results are plotted on the graph in FIG. 9 as line 905.

From this, an estimation of the optimal drop delay time can be determined by determining the drop delay time where the S1 Ratio is maximized. This can be accomplished by viewing the graph in FIG. 9. Alternatively, the plot of S1 Ratio values depicted by line 905 can be approximated using polynomial approximation. In one embodiment, $6^{th}$ degree polynomial approximation is used to determine an equation that best fits the set of S1 Ratio values depicted by line 905. From the approximation, the maximum value for S1 Ratio can be mathematically determined, where the maximum value for S1 Ratio represents the optimal delay time.

According to the above, in the flow cytometer 1, the control unit 7 calculates the delay time by referring to the adjacent information relating to the sum of intensity of each image region S0, S1, S2 of the droplets. In this manner, in the flow cytometer 1, the optimal drop delay time will represent the drop delay at the point where the last attached droplet contains the largest number of beads, and at the same time, the former and latter droplets contain the least number of beads. Therefore, it is possible to accurately and automatically apply the charge to the droplets.

Furthermore, the first delay time determination method, which is an example of the present step S7 is used favorably in a case in which the detection of the microparticles contained in the sample is performed in the microchip 2 and the application of charge to the droplet D is performed in air. In other words, the speed of the sample varies between inside the microchip 2 and in the air, and therefore in a case in which it is necessary to adjust the timing at which the charge is applied to the sample, it is particularly effective to determine the delay time using the first delay time determination method.

2-7-2 Second Fine Delay Time Determination Method

Next, description will be given of the second delay time determination method with reference to FIG. 10, in which the delay time is determined by finding the minimum of the sum of intensities of image regions S0 and S2. In this method, all of the steps are carried out the same as in the first method (Step 2-7-1), however here, the optimal drop delay value is determined by finding the minimum of the sum of the intensity values when image regions S0 and S2 are combined. In FIG. 10, line 1000 represents the measured sums of intensity of region S0 and line 1002 represents the measured sums of intensity of region S2.

2-7-3 Third Fine Delay Time Determination Method

Next, description will be given of the third delay time determination method with reference to FIG. 11, in which the delay time is determined by finding the maximum of the sum of intensities of image region S1. In this method, all of the steps are carried out the same as in the first method (Step 2-7-1), however here, the optimal drop delay value is determined by finding the maximum of the sum of intensity values of image region S1. In FIG. 11, line 1101 represents the measured sums of intensity of region S1.

2-7-4 Alternative Features

The steps above describe methods of determining when the maximum number of detected particles are in the last attached droplet (i.e., image region S1). In these embodiments, the Microparticle Sorting Step (discussed in detail below at S8) applies a charge to the particles in the droplet when the particles are located in the last attached droplet and the charged particles are then sorted based on this charge. However, due to background noise or other issues, clearer and higher quality calibration images may be obtained at alternative locations in the droplet stream. If that is the case, and the fine drop delay time is determined by a set of particles not located in the last attached droplet, the fine delay time necessary to determine when the particles are in the last attached droplet may be determined by simply adding or subtracting delay times from the acquired fine delay time. For example, if the fine delay time is determined by maximizing the number of particles in a droplet that is two droplets upstream from the last attached droplet, the calculated fine delay time merely needs to have two delay times added thereto to determine the fine delay time for when the particles are located in the last attached droplet. In one embodiment, highest quality calibration images are obtained the last attached droplet is defined as image region S2, the droplet above is image region S1, and the droplet above that is image region S0, where the fine delay time is determined by maximizing the sum of intensity in image region S1. In this embodiment, once the fine delay time is determined that maximizes the sum of intensity at image region S (corresponding to the number of desired particles in the droplet), one delay time is simply added thereto to get the delay time for maximizing the number of desired particles in the last attached droplet.

2-8 Microparticle Sorting Step S8

FIG. 11 is flow chart for illustrating step S8 in which microparticles such as cells are sorted in the flow cytometer 1. In the microparticle sorting step S8, the flow cytometer 1 performs sorting of the droplets containing microparticles such as cells based on the delay time which is determined in steps S1 to S7 described above. A trajectory direction discrimination step includes the processes of "the microparticle detection step S-8-1" and "the droplet discharge and charge application step S-8-2". Description will be given of each process below.

2-8-1 Microparticle Detection Step

First, in the present step S-8-1, the detection unit 3 detects the microparticles. The detection method may be performed in the same manner as the process in step S1 described above.

2-8-2 Droplet Discharge and Charge Application Step S-8-2

Next, in the present step S-8-2, once the determined delay time has elapsed from the time at which the microparticles such as cells are detected by the detection unit 3, the control unit 7 outputs a signal to the charge unit 11 for performing charge application on the droplets containing the microparticles (refer to FIG. 11). Furthermore, the charge unit 11 applies a charge to the droplets.

It should be understood by those skilled in the art that various modifications, combinations, sub-combinations and alterations may occur depending on design requirements and other factors insofar as they are within the scope of the appended claims or the equivalents thereof.

What is claimed is:

1. A microparticle sorting apparatus comprising:

a detector configured to detect microparticles flowing through a flow path;

an imaging device configured to obtain an image of a droplet containing at least one of the microparticles, wherein the droplet is discharged from an orifice provided on the flow path creating a droplet stream; and a controller configured to:

control the imaging device to obtain the image, the image including a first image region having a first plurality of sub-areas, a second image region having a second plurality of sub-areas, and a third image region having a third plurality of sub-areas;

obtain the image at a plurality of different times;

for each of the plurality of different times, determine an intensity of brightness for each of the first plurality of sub-areas, each of the second plurality of sub-areas, and each of the third plurality of sub-areas;

add the intensity of brightness for each of the first plurality of sub-areas to obtain a first image region sum of intensity, the intensity of brightness for each of the second plurality of sub-areas to obtain a second image region sum of intensity, and the intensity of brightness for each of the third plurality of sub-areas to obtain a third image region sum of intensity, thereby obtaining a first image region sum of intensity, a second image region sum of intensity, and a third image region sum of intensity at each of the plurality of different times;

determine a delay time from the time at which the detector detects microparticles flowing through the flow path to the time at which the first image region sum of intensity is at a maximum by determining a maximum sum of intensity characteristic, the maximum sum of intensity characteristic being based, at least in part, on: the first image region sum of intensity, the second image region sum of intensity, and the third image region sum of intensity; and set a timing for applying a charge to the droplets based on the delay time.

2. The microparticle sorting apparatus of claim 1, wherein the first image region is associated with a last attached droplet of the droplet stream.

3. The microparticle sorting apparatus of claim 1, wherein the first image region is associated with a droplet following a last attached droplet of the droplet stream.

4. The micropraticle sorting apparatus of claim 3, wherein the delay time is based on a droplet clock cycle;

wherein the charge is applied to the last attached droplet; and wherein +1 droplet clock cycle is added to the delay time to obtain the delay time for the last attached droplet.

5. The microparticle sorting apparatus of claim 1, wherein the plurality of different times occur at intervals based on a droplet clock cycle;

wherein the droplet clock cycle consists of 360 degrees and the plurality of different times occur at either twenty or forty degree intervals spanning three droplet clock cycles.

6. The microparticle sorting apparatus of claim 5, wherein the maximum sum of intensity characteristic is determined using a first image region sum of intensity ratio, including the first image region sum of intensity, the second image region sum of intensity, and the third image region sum of intensity:

$$\text{first image region sum of inteisity ratio} = \left(\frac{\text{first image region sum of intensity}}{\text{first} + \text{second} + \text{third image region sums of intensity}}\right).$$

7. A microparticle sorting apparatus comprising:

a detector configured to detect microparticles flowing through a flow path;

an imaging device configured to obtain an image of a droplet containing at least one of the microparticles, wherein the droplet is discharged from an orifice provided on the flow path; and a non-transitory storage medium that stores computer readable instructions that when executed by processing circuitry cause the processing circuitry to:

divide the image into a plurality of image regions, and determine a delay time based on a maximum sum of intensity characteristic, the maximum sum of intensity characteristic being based, at least in part, on a first image region sum of intensity, a second image region sum of intensity, and a third image region sum of intensity.

8. The microparticle sorting apparatus of claim 7, wherein each image region includes at least one microparticle.

9. The microparticle sorting apparatus of claim 7, wherein the image includes a plurality of images obtained in a plurality of difference times.

10. The microparticle sorting apparatus of claim 9, wherein the plurality of different times is based on a droplet clock cycle and spans three droplet clock cycles.

11. The microparticle sorting apparatus of claim 10, wherein each droplet clock cycle consists of three hundred and sixty degrees and wherein the plurality of different times occur at twenty degree intervals.

12. The microparticle sorting apparatus of claim 10, wherein each droplet clock cycle consists of three hundred and sixty degrees and wherein the plurality of different times occur at forty degree intervals.

13. The microparticle sorting apparatus of claim 10, each droplet clock cycle consists of three hundred and sixty degrees and wherein the plurality of different times occur at sixty degree intervals.

14. The microparticle sorting apparatus of claim 7, wherein the delay time is determined by minimizing at least one of: the second image region sum of intensity, or the third image region sum of intensity.

15. The microparticle sorting apparatus of claim 7, wherein the maximum sum of intensity characteristic is determined by computing a first image region ratio, including the first image region sum of intensity, the second image region sum of intensity, and the third image region sum of intensity:

$$\text{first image region ratio} = \left(\frac{\text{first image region sum of intensity}}{\text{first} + \text{second} + \text{third image region sums of intensity}}\right).$$

16. The microparticle sorting apparatus of claim 15, wherein the first image region, the second image region and the third image region are successive regions.

17. The microparticle sorting apparatus of claim 1, where the first image region is associated with a last attached droplet.

18. The microparticle sorting apparatus of claim 14, where the second image region is adjacent to the first image region and the third image region is adjacent to either the second image region or the first image region.

19. The microparticle sorting apparatus of claim 15, wherein the first image region is associated with a droplet following a last attached droplet in a droplet stream.

20. The microparticle sorting apparatus of claim 19, where the second image region is adjacent to the first image region and the third image region is adjacent to either the second image region or the first image region.

* * * * *